United States Patent [19]

Bright

[11] Patent Number: 5,616,585
[45] Date of Patent: Apr. 1, 1997

[54] PYRIDOPYRAZINE DERIVATIVES FOR TREATING ALCOHOL AND NICOTINE ABUSE AND ADDICTION

[75] Inventor: Gene M. Bright, Groton, Conn.

[73] Assignee: Pfizer Inc., New York, N.Y.

[21] Appl. No.: 377,874

[22] Filed: Jan. 25, 1995

Related U.S. Application Data

[63] Continuation of Ser. No. 969,843, filed as PCT/US91/03749, May 28, 1991, and PCT/US90/03708, Jun. 29, 1990, abandoned.

[51] Int. Cl.$^6$ .......................... A61K 31/495; A61K 31/50
[52] U.S. Cl. .......................... 514/249; 514/810; 514/811; 514/812; 514/813
[58] Field of Search ................... 514/249, 810, 514/811, 812, 813

[56] References Cited

U.S. PATENT DOCUMENTS 5,122,525  6/1992  Bright et al. ............................ 514/249

FOREIGN PATENT DOCUMENTS 380217  8/1990  European Pat. Off. .

OTHER PUBLICATIONS

Chemical Abstracts 114 (9): 81886r, Bright, G.M. et al. (1990).
G. D. Tollefson, British Journal of Psychiatry 159, 34–39 (1991).
C. C. Chen, Japanese Journal of Psychiatry and Neurology 46(1), 197–203 (1992).
E. D. Levin, Pharmacology Biochemistry and Behaviour 44, 51–61 (1993).
E. B. Ribeiro, Brain Research 621, 311–318 (1993).

*Primary Examiner*—Marianne M. Cintins
*Assistant Examiner*—M. Moezie
*Attorney, Agent, or Firm*—Peter C. Richardson; Paul H. Ginsburg; Bryan C. Zielinski

[57] ABSTRACT

Racemic or optically active pyrido[1,2-a]pyrazine derivatives of the formula

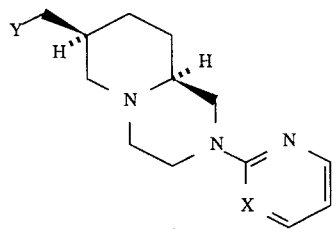

wherein X is N or CH and Y represents one of certain pyrazolo, triazolo, tetrazolo or cyclic imido radicals are useful in the treatment of abuse of and/or addiction to such substances as narcotics, alcohol and nicotine.

18 Claims, No Drawings

PYRIDOPYRAZINE DERIVATIVES FOR TREATING ALCOHOL AND NICOTINE ABUSE AND ADDICTION

This is a continuation of application Ser. No. 07/969,843, filed as PCT/US91/03749 May 28, 1991, and PCT/US90/03708 on Jun. 29, 1990, now abandoned.

BACKGROUND OF THE INVENTION

The present invention is directed to the use of certain racemic and optically active pyrido[1,2-a]-pyrazine derivatives, also described as bis-azabicyclic compounds and defined by the formula (I) below in the treatment of abuse of and addiction to such substances as narcotics, alcohol, nicotine and amphetamines. The compounds of the formula (I) and their use in the treatment of anxiety and depression are the subjects of copending International application nos. PCT/US89/00275, filed Jan. 26, 1989, and PCT/US89/03811, filed Sep. 1, 1989.

Recently a number of 1-(2-pyrimidinyl)-4-[4-(cyclic-imido)butyl]piperidine derivatives have been disclosed as anxiolytic agents which are generally lacking sedative activity. Among these are buspirone, where the cyclic-imido group is 4,4-tetramethylene-piperidine-2,6-dion-1-yl (Wu et al., U.S. Pat. Nos. 3,717,634 and 3,907,801; Casten et al., U.S. Pat. Nos. 4,182,763); gepirone, where the group is 4,4-dimethylpiperidine-2,6-dion-1-yl (Temple, Jr., U.S. Pat. No. 4,423,049); and ipsapirone, where the group is 1,1-dioxobenzo[d]isothiazol-3(2H)-on-2-yl (Dompert et al., German patent publication 3,321,969-Al). See also Ishizumi et al., U.S. Pat. Nos. 4,507,303 and 4,543,355; Freed et al., U.S. Pat. 4,562,255; Stack et al., U.S. Pat. No. 4,732,983; New et al., U.S. Pat. No. 4,524,026; and Stack, U.S. Pat. No. 4,788,290.

Such agents as busipirone and gepirone have now been shown to possess antidepressant activity [Schweizer et al., Psychopharm. Bull., v. 22, pp. 183–185 (1986); Amsterdam et al., Current. Therap. Res., v. 41, pp. 185–193 (1987); and Stack, U.S. Pat. No. 4,788,290]; and most recently, to be of value in the treatment of substance addiction, such as over-eating, tobacco addiction and drug abuse (published European patent application EP-A-356,997).

The present bis-aza-bicyclic compounds generally show minimal in vivo stimulation of dopaminergic systems, reflective of reduced or minimal neurological side effects in the clinical use of these compounds.

SUMMARY OF THE INVENTION

The present invention is directed to the use of certain bis-aza-bicyclic compounds, vii., racemic or optically active compounds of the formula (I)

and the pharmaceutically acceptable acid addition salts thereof, wherein

X is N or CH;

Y is $SCH_2$, $OCH_2$, $-Y^1(CH_2)_n$ or $Y^1(CH_2)_n$ substituted on carbon with up to 2 methyl groups;

n is 1 or 2; and $y^1$ is $CH_2$, NH or $NCH_3$;

in the treatment of substance abuse or addiction in a mammal, including man.

In the compounds of the formula (I), for ease of preparation and good activity, Y is preferably A particularly preferred compound is that wherein Z is $Y^1(CH_2)_n$, $Y^1$ is $CH_2$, n is 1 and X is N.

The nomenclature employed herein is that of the I.U.P.A.C., Nomenclature of Organic Chemistry, 1979 Ed., Pergammon Press, New York. Alternative names for the nucleus of the present bis-aza-bicyclic compounds are perhydro-1H-pyrido[1,2-a]pyrazine, 2,4a-diazaperhydronaphthalene, and 1,4-diazabicyclo[5.5.0]decane.

Said pharmaceutically acceptable acid addition salts include but are not limited to those with HCl, $HNO_3$, $H_2SO_4$, $H_3PO_4$, $pCH_3C_6H_4SO_3H$ or $HOOCCH_2CH_2COOH$. These salts are prepared by conventional methods, for example, by combining molar equivalent amounts of a compound of the formula (I) and the appropriate acid in a solvent from which the desired salt is of low solubility and precipitates directly, or from which the salt can be isolated by concentration or addition of a non-solvent.

The present invention also encompasses pharmaceutical compositions comprising an amount of a compound of the formula (I) which is effective in the treatment of substance abuse or addiction.

DETAILED DESCRIPTION OF THE INVENTION

The compounds of the above formula (I) are readily prepared by a number of methods. One general method, which is the preferred method for all racemic compounds and the preferred method for optically active compounds when Y is other than an imido group, is to displace the sulfonate ester group of a racemic or optically active compound of the formula

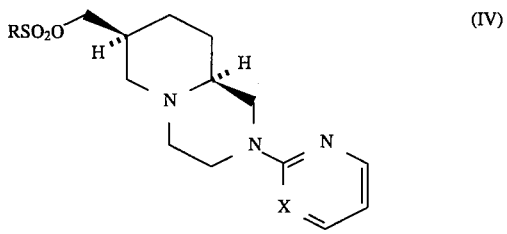

with an anion Y⁻, wherein R, X and Y are as defined above, and Y⁻ represents the anion of a salt MY where M is most simply an alkali metal such as sodium. When the required salt is not available commercially, as is most frequently the case, it is convenient to form the required salt in situ in the form of the sodium salt, e.g., irreversibly by the action of sodium hydride on the compound of the formula Y—H; or reversibly by reaction with a base such as $Na_2CO_3$ which is not itself nucleophilic. This process is representative of such displacement reactions in general. It is generally carried out in a reaction inert-solvent, preferably one which is aprotic and certainly one which is less acidic than the compound Y—H. Particularly useful solvents in the present instance are acetonitrile and dimethylformamide. Temperature is not generally critical in this process, but, in order to achieve complete conversion within a reasonably short period of time, elevated temperatures, e.g., 90°–120° C., are generally preferred. Also for the purpose of forcing this second order displacement reaction to completion within a reasonable period of time, a molar excess of one of the reactants, usually the more readily available salt, MY, is generally employed in this process. Methyl is the preferred value of R in this process, for ease of preparation of the mesylate ester and for the facile displacement of the mesylate anion. The product is isolated by conventional methods of concentration, evaporation, extraction, chromatography and crystallization, with, if direct formation of an acid addition salt is desired, addition of an appropriate acid in an appropriate amount, e.g., addition of one molar equivalent of HCl if the mono-hydrochloride salt is desired.

As used in the preceding paragraph and elsewhere herein, the expression "reaction-inert" solvent refers to a solvent which does not interact with reactants, reagents, intermediates or products in a manner which adversely affects the yield of the desired product.

A second general method for preparation of compounds of the formula (I) is to directly couple an alcohol of the formula

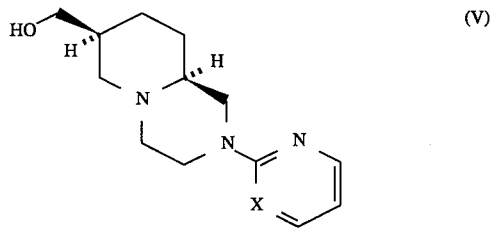

with the heterocycle or imide of the formula YH, where again X and Y are as defined above. The preferred coupling reagent is an approximately 1:1 molar mixture diethyl azodicarboxylate and triphenylphosphine. Usually, about 2 to 2.1 molar equivalents of these reagents are used in coupling equimolar amounts of YH and the alcohol (V). The preferred solvents are relatively polar ethers such as tetrahydrofuran, dioxane or 1,2-dimethoxyethane, the first of these being particularly well-suited. Temperature is not critical, although somewhat elevated temperatures (e.g., the reflux temperature of tetrahydrofuran) are preferred, in order to achieve complete reaction in a reasonable period of time.

The compounds of the formula (I) wherein the group Y is an imido group are also generally prepared from the corresponding amine of the formula

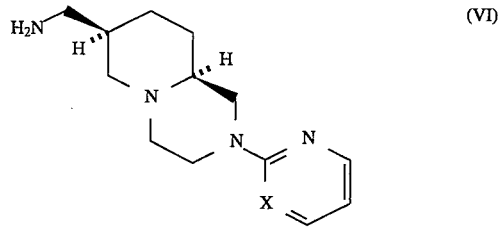

by the action of an anhydride of the formula

wherein X and Z are as defined above. This is the preferred method for preparation of optically active compounds of the formula (I) when Y is an imido group (excluding those compounds wherein the group Z contains an NH group, where the anhydride has the potential to polymerize). According to this alternative method, the amine (VI) and the anhydride (VII), generally in about molar equivalents, are heated to about 100°–160° C. in a reaction inert solvent. Particularly well suited as solvent here are mixed xylenes boiling in the range of about 138°–142° C. The reaction is then conveniently carried out at the reflux temperature of said mixed xylenes.

The required racemic and optically active starting materials of the above formulas (IV), (V) and (VI) are prepared via the synthetic routes summarized in Flowsheet 1. While the overall route and the various intermediates are novel, the individual chemical steps are generally analogous to known chemical transformations. Generally suitable conditions are found in the prior art. Particularly well-suited conditions are exemplified below.

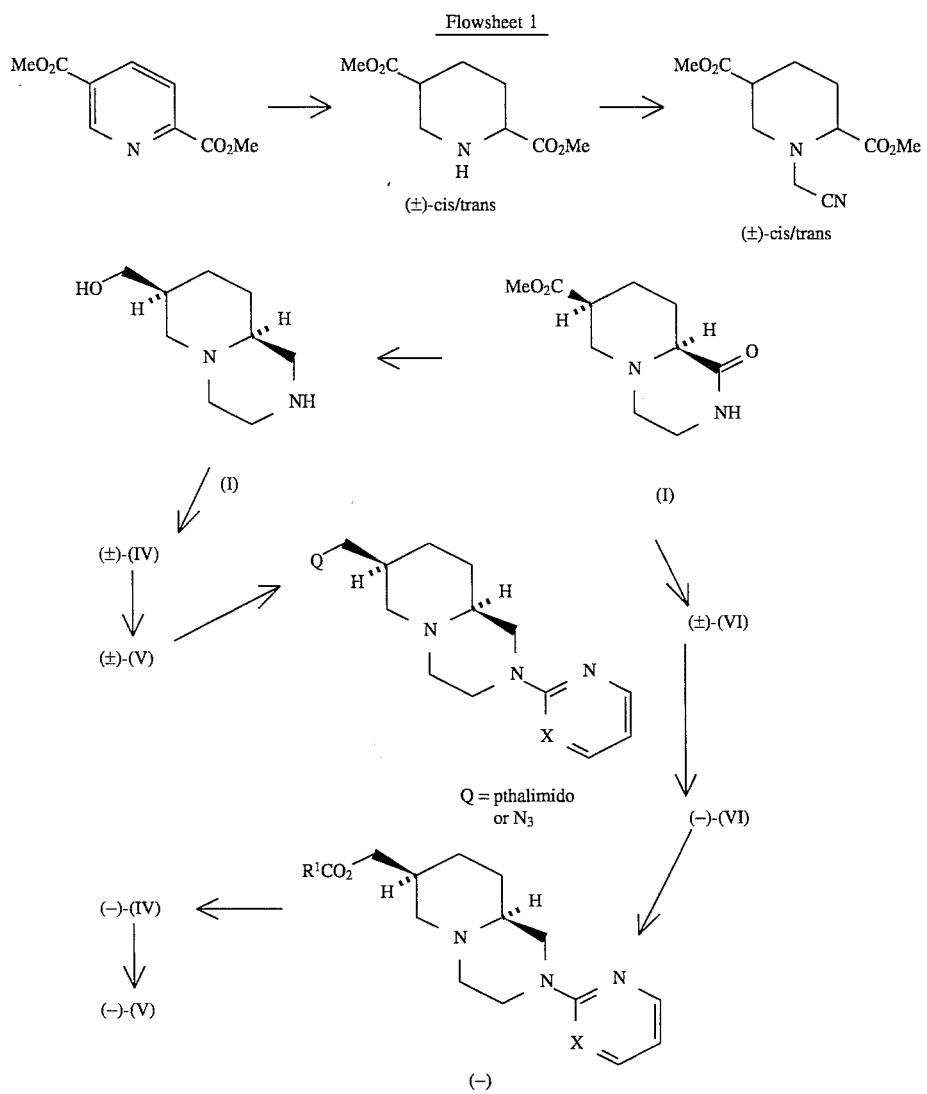

Flowsheet 1

Q = pthalimido or N₃

The value of the present compounds in the treatment of substance abuse or addiction is determined by the use of animal models which are well-established in the art. For example, see:

- In General: Schuster, C. R., and Johansen, C. E., The Use of Animal Models for the Study of Drug Abuse. In: R. J. Gibbens, Y. Israel, H. Kalant, R. E. Popham, W. Schmidt, and R. G. Smart (Eds.) Research Advances in Alcohol and Drug Problems, Vol. 1, pp. 1–31, John Wiley and Sons, New York, 1974.
- Re Stimulants: Johansen, C. E., and Schuster, C. R., Procedures for the Preclinical Assessment of Abuse Potential of Psychotropic Drugs in Animals. In: Predicting Dependence Liability of Stimulant and Depressant Drugs, Eds. Travis Thompson and Klaus Unna. pp. 203–229 University Park Press, Baltimore, 1977.
- Re Opiates: Weeks, J. R., Experimental Morphine Addiction: Method for Automatic Intravenous Injections in Unrestrained Rats, Science, 138: 143–144 (1962).
- Re Alcohol: Altshuler, H. L., Phillips, P. E., and Feinhandler, D. A., Alteration of Ethanol Self-administration by Naltrexone, Life Sci., 26: 679–688 (1980).
- Re Nicotine: Goldberg, S. R., Spealman, R. D., and Goldberg, D. M., Persistent High-rate Behavior Maintained by Intraveous Self-administration of Nicotine, Science, 214: 573–575 (1981).

For use in treating substance abuse and alleviating the symptoms of anxiety or addiction in a human subject, a compound of the formula (I), or a pharmaceutically-acceptable salt thereof, is administered in an amount of about 2–200 mg/day, in single or divided daily doses. In particular cases, dosages outside that range are prescribed at the discretion of the attending physician. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), or a salt thereof, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1 cis-2-(2-Pyrimidinyl)-7-(succinimidomethyl)-2,3,4, 6,7,8,9,9a-octahydro-1H-pyrido[1,2-a]pyrazine Method A A flame-dried flask fitted with magnetic stirring and a nitrogen inlet was charged with succinimide (0.95 g; 9.6 mmol) in dry dimethylformamide (25 ml). Sodium hydride (0.49 g of 60% mineral oil dispersion; 12.2 mmol) was added all at once, and the resulting mixture was stirred and heated at 70° C. for 1 hour. cis-7-(Methanesulfonyloxymethyl)-2-(2-pyrimidyl)-2,3,4,6,7,8,9,9a -octahydro-1H-pyrido[1,2-a]pyrazine (1.56 g; 4.8 retool) was added, and the stirred mixture heated at 110° C. for 18 hours. Concentration in vacuo afforded a solid, which was dissolved in 25 ml of $CH_2Cl_2$. An equal volume of water was added, and the pH of the well-stirred mixture was adjusted to 2.0 (6N HCl). The separated organic phase was extracted a second time with an equal volume of water at pH 2.0. Finally, the organic phase was extracted with an equal volume of water at pH 10.0 (saturated $Na_2CO_3$). The basic aqueous phase was separated, and extracted 2×150 ml $CH_2Cl_2$. The latter organic layers were combined, treated with activated carbon, dried ($Na_2SO_4$) and concentrated in vacuo to afford a colorless amorphous foam, which was crystallized from 35 ml of isopropanol to afford 1.14 g (72%) of title compound as colorless crystals, mp 183°–184° C. TLC Rf 0.43 (9:1 $CH_2Cl_2$: $CH_3OH$). HRMS 329.1906, calcd. 329.1854.

$^{13}$C-NMR(250MHz, CDCl$_3$) delta 177.4, 161.4, 157.7, 109.6, 61.0, 57.9, 54.7, 48.8, 43.5, 40.7, 32.2, 28.1 24.9, 24.4

Method B

To a magnetically stirred solution of triphenylphosphine (262 mg, 1.0 retool) and diethylazodicarboxylate (0.174 ml, 192 mg, 1.05 mmol) in 8 ml of dry tetrahydrofuran, a solution consisting of succinimide (99 mg, 1.0 mmol) and cis-7-(hydroxymethyl)-2-(2-pyrimidinyl)-2,3,4,6,7,8,9,9a-octahydro-1H-pyrido[1,2-a]pyrazine(248 mg, 1.0 mmol) in 20 ml of dry tetrahydrofuran was added dropwise over one hour. The reaction was refluxed for 18 hours; and then concentrated in vacuo to an oil. The oil was dissolved in methylene chloride/water mixture (35 ml of each). The pH of the well-stirred mixture was then adjusted to 2 with 6N HCl, and the phases were then separated. The organic phase was combined with 10 ml of water, and the pH of the mixture likewise adjusted to 2. The two acidic aqueous extracts were combined and stirred with an equal volume of methylene chloride while the pH was adjusted to 10 with saturated $Na_2CO_3$. The phases were separated and the aqueous phase was extracted twice with fresh 50 ml portions of methylene chloride. The three organic extracts were combined, treated with activated carbon, dried ($Na_2SO_4$) and stripped to an oil which was crystallized from isopropanol to yield 31 mg (9.5%) of present title product identical with that of Method A.

Method C

A solution of cis-7-(aminomethyl)-2-(2-pyrimidinyl)-2,3, 4,6,7,8,9,9a-octahydro-1H-pyrido[1,2-a]pyrazine(149 mg, 0.6 retool), succinic anhydride (60 mg, 0.6 mmol) in xylenes (9 ml, constant boiling range 138°–142° C.) was refluxed for 18 hours. The reaction was concentrated in vacuo to an oil, which was taken up in methylene chloride (30 ml). An equal volume of water was added, and the pH of the well-stirred mixture adjusted to 2.0 (6N HCl). The phases were separated, and the organic phase was extracted with a fresh portion of water at pH 2. The combined acidic extracts were stirred with methylene chloride (40 ml) with the pH adjusted to 10.0 (saturated $Na_2CO_3$). The phases were separated, and the aqueous phase was extracted twice with fresh 40 ml portions of methylene chloride. The basic organic extracts were combined, treated with activated carbon, dried ($Na_2SO_4$) and concentrated in vacuo to a solid which was crystallized from 7 ml of isopropanol to yield 164 mg (83%) of the title compound as colorless crystals, identical with the products of methods A and B.

EXAMPLE 2 cis-7-(Substituted methyl)-2-(2-pyrimidinyl)-2,3,4,6, 7,8,9,9a-octahydro-1H-pyrido[1,2-a]pyrazines The following additional title compounds were prepared according to Method A of the preceding Example, substituting the appropriate imide or heterocycle for succinimide. Shown is the substituent, its yield, and its properties. All $^{13}$C-NMR indicate values at 300 MHz in CDCl$_3$, unless otherwise specified. If unspecified, the TLC eluant was 9:1 $CH_2Cl_2$:$CH_3OH$ on 0.25 mm silica gel 60F$_{254}$ plates. 3,3, 4-Trimethylsuccinimido (9.7%); crystallized from ethyl acetate:hexane; TLC Rf 0.58; HRMS 371.2274, calcd. 371. 2321.

$^{13}$ C-NMR 183.2, 179.4, 161.3, 157.6, 109.5, 60.9, 57.9, 54.7, 48.8, 45.8, 43.5, 43.0, 40.2, 32.3, 32.1, 24.7, 24.3, 21.2, 10.2

Thiazolidine 2,4-dion-3-yl (19.5%); amorphous; HRMS 347.1478, calcd. 347.1426

$^{13}$C-NMR 171.9, 171.6, 161.3, 157.6, 109.6, 60.9, 57.8, 54.7, 48.9, 43.9, 43.6, 33.7, 32.2, 24.9, 24.5 meso-3,4-Dimethylsuccinimido (50%); crystallized from $CH_2Cl_2$:isopropanol; mp 141°–142° C.; TLC Rf 0.56.

$^{13}$C-NMR (250 MHz) 179.7, 161.5, 157.7, 109.5, 61.1, 58.0, 54.8, 49.0, 43.7, 43.0, 40.6, 32.3, 25.0, 24.5, 15.2

3-Methylsuccinimido (46.5%); crystallized from $CH_2Cl_2$:isopropanol; mp 168°–172° C.; TLC Rf 0.51; HRMS 344.2011, calcd. 344.2086.

$^{13}$C-NMR (250 MHz) 180.7, 176.7, 161.5, 157.1, 109.6, 61.1, 58.1, 54.8, 49.0, 43.7, 40.7, 36.5, 34.6, 32.3, 25.0, 24.5, 17.0

3-Methylimidazolidine-2,5-dione-1-yl (28.9%); crystallized from ether; mp 106°–108° C.; TLC Rf 0.42; HRMS 344.1968, calcd. 344.1960.

$^{13}$C-NMR 170.0, 161.3, 157.7, 157.1, 109.5, 61.0, 57.9, 54.8, 51.6, 48.9, 43.6, 40.9, 32.5, 29.6, 24.8, 24.4

3-Azabicyclo[3.2.1]octane-2,4-dion-3-yl (21%); TLC Rf 0.44; HRMS 369.2205, calcd. 369.2167.

$^{13}$C-NMR 161.2, 157.6, 109.4, 60.9, 58.3, 54.7, 48.8, 44.8, 44.7, 43.5, 40.5, 32.5, 32.4, 27.1(2), 24.8, 24.7

Piperidine-2,6-dion-1-yl (10%); crystallized from $CH_2Cl_2$: hexane; mp 146°–148° C.; TLC Rf 0.37; HRMS 343.2011, calcd. 343.2011.

$^{13}$C-NMR 172.7, 161.4, 157.7, 109.5, 61.1, 58.5, 54.8, 48.9, 43.6, 41.4, 33.0, 32.7, 25.0, 24.8, 17.2

4,4-Dimethylpiperidine-2,6-dion-1-yl (14.5%); crystallized from ethyl acetate; mp 212°–213° C.; TLC Rf 0.51; HRMS 371.2276, calcd. 371.2322.

$^{13}$C-NMR 172.2, 161.4, 157.7, 109.5, 61.1, 58.6, 54.9, 48.9, 46.5, 43.6, 41.5, 32.9, 29.0, 27.7, 25.1, 24.8

8-Aza-spiro[4.5]decane-7,9-dion-8-yl (31.9%); crystallized from isopropanol; mp 172°–173° C.; TLC Rf 0.49; HRMS 397.2450, calcd. 397.2480.

$^{13}$C-NMR (250 MHz) 172.4, 161.4, 157.7, 109.5, 61.1, 58.5, 54.9, 48.9, 45.0, 43.5, 41.5, 39.4, 37.6, 32.9, 25.0, 24.7, 24.2

5,5-Dimethyloxazolidine-2,4-dione-3-yl (20.8%); crystallized from ethyl acetate:hexane; mp 162°–163° C.; TLC Rf 0.65; HRMS 359.1936, calcd. 359.1957.

$^{13}$C-NMR 176.1, 161.2, 157.5, 154.6, 109.5, 83.2, 60.8, 57.5, 54.6, 48.8, 43.5, 41.5, 32.0, 24.6, 24.3, 23.5, 23.4

Imidazolidine-2,5-dione-1(33.6%); crystallized from CH$_2$Cl$_2$: ether; mp 191°–192° C.; TLC Rf 0.30; HRMS 330.1804, calcd. 330. 1804

$^{13}$C-NMR 171.8, 161.3, 159.1, 157.6, 109.6, 61.0, 57.7, 54.7, 48.9, 46.4, 43.5, 40.4, 32.4, 24.7, 24.4

3,3-Dimethylsuccinimido (55.6%); crystallized from CH$_2$Cl$_2$: isopropyl ether; mp 145°–147° C.; TLC Rf 0.53; HRMS 357. 2126, calcd. 357. 2164.

$^{13}$C-NMR 183.4, 175.9, 161.3, 157.6, 109.5, 61.0, 57.9, 54.7, 48.8, 43.5(2), 40.4, 39.8, 32.2, 25.6, 24.8, 24.4

Pyrazolo (23.8%); crystallized from ether; mp 86°–88° C.; TLC Rf 0.46; HRMS 298.1895, calcd. 298.1906

$^{13}$C-NMR 161.3, 157.8, 139.4, 129.8, 109.7, 104.8, 61.0, 56.6, 54.7, 53.0, 49.0, 43.6, 34.6, 25.0, 24.7

1,2,4-Triazol-1-yl (62.3%); crystallized from ethyl acetate:hexane; mp 150°–152° C.; TLC Rf 0.37; HRMS 299.1853, calcd. 299.1858.

$^{13}$C-NMR 161.3, 157.6, 152.0, 145.7, 109.8, 60.9, 56.2, 54.6, 50.4, 48.9, 43.6, 33.9, 24.9, 24.6

4,4-Dimethylimidazolidine-2,5-dion-1-yl (25%); crystallized from CH$_2$Cl$_2$:ether, mp 189°–190° C.; TLC Rf 0.35; HRMS 358.2074, calcd. 358.2000.

$^{13}$ $^{C-NMR}$ 177.8, 161.2, 157.6, 156.9, 109.5, 60.9, 58.4, 57.6, 54.6, 48.8, 43.5, 40.0, 32.3, 25.0, 24.6, 24.3

Tetrazol-2-yl (30.5%); amorphous; TLC Rf 0.64; HRMS 300.1792, calcd. 300.1809.

$^{13}$C-NMR 161.2, 157.5, 152.8, 109.6, 60.8, 56.6, 54.5, 54.1, 48.8, 43.5, 34.3, 24.9, 24.4

4,5-Dihydro-1H, 3H-pyrimidine-2,6-dion-1-yl (46%); crystallized from isopropanol:ether; mp 190°–192° C.; TLC Rf 0.36; HRMS 344.1919, calcd. 344.1960.

$^{13}$C-NMR 169.8, 161.4, 157.7, 155.5, 109.5, 61.1, 58.4, 54.9, 48.9, 43.6, 42.0, 35.3, 33.0, 31.8, 25.4, 24.8

5-Methyl-4,5-dihydro-1H, 3H-pyrimidine-2,6-dione-1-yl (23%); crystallized from ethanol; mp 201°–202° C.; TLC Rf 0.35; HRMS 358.2118, calcd. 358.2117.

$^{13}$C-NMR 172.9, 161.4, 157.7, 155.4, 109.5, 61.1, 58.4, 54.9, 48.9, 43.6, 42.4, 42.3, 42.1, 35.8, 33.2, 33.0, 24.9, 13.4 (extra peaks due to diastereomers)

4-Methyl-4,5-dihydro-1H, 3H-pyrimidine-2,6-dione-1-yl (55%); crystallized from CH$_2$Cl$_2$:ether; mp 202°–208° C.; TLC Rf 0.38; HRMS 358.2128, calcd. 358.2117.

$^{13}$C-NMR 169.6, 161.4, 157.7, 155.2, 109.5, 61.1, 58.4, 54.9, 48.9, 43.5, 42.4, 42.0, 39.3, 33.2, 32.9, 24.9, 24.8, 20.8 (excess peaks due to diastereomers)

EXAMPLE 3 cis-7-(Substituted methyl) -2-(2-pyridyl)-2,3,4,6,7,8, 9,9a-octahydro-1H-pyrido[1,2-a]pyrazines Substituting the analogous 2-(2-pyridyl)mesylate ester for the 2-(2-pyrimidinyl)mesylate ester, the following additional title compounds (specified as in the preceding Example) were prepared by Method A of Example 1.

3-Methylimidazolidine-2,5-dion-1-yl (8.9%); crystallized from CH$_2$Cl$_2$:isopropyl ether; mp 142°–143° C.; TLC Rf 0.43; HRMS 343.1978, calcd. 343.2018.

$^{13}$C-NMR 170.0, 159.2, 157.0, 147.8, 137.3, 112.8, 106.8, 60.7, 57.7, 54.6, 51.5, 50.5, 45.0, 40.7, 32.5, 29.5, 24.7, 24.5

4,4-Dimethylpiperidine-2,6-dion-1-yl (31.7%); crystallized from ether; mp 134°–135° C.; HRMS 370.2321, calcd. 370.2368.

$^{13}$C-NMR 172.2, 159.3, 147.9, 137.4, 112.9, 106.9, 60.9, 58.5, 54.8, 50.6, 46.5, 45.0, 41.5, 32.9, 29.1, 27.7, 25.1, 24.9

Succinimido (36.3%); crystallized from CH$_2$Cl$_2$:ether; mp 164°–165° C.; TLC Rf 0.41; HRMS 328.1880, calcd. 328.1899.

$^{13}$C-NMR 177.4, 159.2, 147.8, 137.3, 112.9, 106.8, 60.7, 57.9, 54.6, 50.5, 45.0, 40.6, 32.1, 28.1, 24.8, 24.5

8-Azospiro[4.5]decane-7,9-dion-8-yl (25.3%); TLC Rf 0.42 (ethyl acetate); HRMS 396.2562, calcd. 396.2525.

$^{13}$C-NMR 172.4, 159.3, 147.9, 137.3, 112.9, 106.9, 60.9, 58.5, 54.8, 50.6, 45.0(2), 41.5, 39.3, 37.6, 32.9, 25.0, 24.9, 24.2

5,5-Dimethyloxazolidine-2,4-dion-3-yl (27.3%); crystallized from CH$_2$Cl$_2$:ether; mp 171°–173° C.; HRMS 358.2040, calcd. 358.2005; TLC Rf 0.56.

$^{13}$C-NMR 176.3, 159.2, 154.8, 147.9, 137.4, 113.0, 106.9, 83.4, 60.7, 57.5, 54.6, 50.6, 45.1, 41.6, 32.1, 24.7, 24.5, 23.6(2)

4-Methylsuccinimido (28%); crystallized from isopropyl alcohol; mp 145°–150° C.; TLC Rf 0.47; HRMS 342.2036, calcd. 342.2056.

$^{13}$C-NMR 180.8, 176.6, 159.3, 147.9, 137.4, 113.0, 106.9, 60.9, 58.0, 54.7, 50.7, 45.1, 40.6, 36.4, 34.6, 32.3, 24.9, 24.6, 16.9

Tetrazolo (36%); amorphous; TLC Rf 0.48 (ethyl acetate); HRMS 299.1778, calcd. 299.1859.

$^{13}$C-NMR 159.1, 152.7, 147.8, 137.3, 113.0, 106.9, 60.6, 56.6, 54.4, 54.1, 50.5, 45.1, 34.3, 24.9, 24.5

4,4-Dimethylsuccinimido (40%); crystallized from ethyl acetate:hexane; TLC Rf 0.45 (ethyl acetate); HRMS 356.2230, calcd. 356.2218

$^{13}$C-NMR 183.5, 176.0, 159.3, 147.9, 137.4, 113.0, 106.9, 60.9, 57.9, 54.7. 50.6, 45.1, 43.6, 40.6, 39.9, 32.3, 25.6(2), 24.8, 24.6

4,4-Dimethylimidazolidine-2,5-dion-1-yl (37%); crystallized from CH$_2$Cl$_2$: isopropyl ether; mp 170°–171° C.; TLC Rf 0.28 (ethyl acetate); HRMS 357.2203, calcd. 357.2166

$^{13}$C-NMR 177.8, 159.3, 157.0, 147.9, 137.5, 113.0, 107.0, 60.9, 58.6, 57.7, 54.7, 50.7, 45.1, 40.3, 32.5, 25.1(2), 24.7, 24.6

Imidazolidine-2,5-dion-1-yl (45%); TLC Rf 0.22; HPMS 329.1903, calcd 329.1854.

$^{13}$C-NMR 171.9, 159.3, 159.1, 147.8, 137.5, 113.1, 107.1, 60.8, 57.7, 54.6, 50.7, 46.5, 45.1, 40.5, 32.4, 24.7, 24.6

1,2,4-Triazol-1-yl (18.7%); crystallized from isopropyl ether:hexane; mp 109°–110° C.; HRMS 298.1943, calcd. 298.1906; TLC Rf 0.37.

$^{13}$C-NMR (250 MHz) 159.2, 152.1, 147.9, 143.6, 137.4, 113.2, 107.0, 60.8, 56.2, 54.6, 50.6, 50.5, 45.2, 33.9, 25.0, 24.7

Piperidine-2,6-dion-1-yl (22.8%); crystallized from CH$_2$Cl$_2$: isopropyl ether; mp 114°–115° C.; TLC Rf 0.44; HRMS 342.2043, calcd. 342.2055.

$^{13}$C-NMR (250 MHz) 172.8, 159.3, 147.9, 137.4, 112.9, 106.9, 60.9, 58.4, 54.8, 50.6, 45.0, 41.5, 33.0, 32.8, 25.0(2), 17.2

4-Methyl-4,5-dihydro-1H,3H-primidine-2,6-dion-1-yl (47%); crystallized from isopropanol; mp 184°–186° C.; TLC Rf 0.35; HRMS 357.2155, calcd. 357.2164.

$^{13}$C-NMR 169.6, 159.3, 155.0, 147.9, 137.4, 112.9, 106.9, 60.9, 58.3, 54.8, 50.6, 45.0, 42.4, 42.1, 39.4, 33.2, 32.9, 24.9, 20.8 (excess peaks due to diastereomers).

5-Methyl-4,5-dihydro-1H,3H-pyrimidine-2,6-dione-1-yl (40%) crystallized from isopropanol; mp 182°–183° C.; TLC Rf 0.34; HRMS 357.2147, calcd. 357.2165.

$^{13}$C-NMR 172.9, 159.4, 155.5, 147.9, 137.4, 113.0, 107.0, 60.9, 58.4, 54.8, 50.6, 45.1, 42.4, 42.3, 42.0, 35.7, 33.3, 33.0, 25.0, 13.4

Dihydro-1H,3H-pyrimidine-2,6-dione-1-yl (67%); crystallized from isopropanol; mp 190°–191° C.; TLC Rf 0.28, HRMS 343.1975, calcd. 343.2011.

$^{13}$C-NMR 169.8, 159.4, 155.4, 147.9, 137.4, 113.0, 107.0, 60.9, 58.3, 54.8, 50.6, 45.1, 42.0, 35.3, 33.0, 31.8, 25.0, 24.9.

Thiazolidine-2,4-dion-3-yl (63%); crystallized from isopropanol; mp 159°–160° C.; TLC Rf 0.47 (19:1 ethyl acetate:CH$_3$OH); HRMS 346.1528, calcd. 346.1463.

$^{13}$C-NMR 171.9, 171.7, 159.3, 148.0, 137.5, 113.1, 107.0, 60.8, 57.8, 54.6, 50.6, 45.1, 44.0, 33.7, 32.2, 24.9, 24.6.

EXAMPLE 4 cis-7-(Succinimidomethyl)-2-(2-pyridyl)-2,3,4,6,7,9,
9a-octahydro-1H-Pyrido[1,2a]pyrazine By method B of Example 1, cis-7-(hydroxymethyl)-2-(2-pyridyl)-2,3,4,6,7,8,9,9a-octrahydro-1H-pyrido[1,2-a]pyrazine (247 mg, 1.0 mmol) and succinimide were converted to 231 mg (70%) of present title product as crystals from isopropyl alcohol, identical to the material prepared in the preceding Example.

EXAMPLE 5 cis-7-[(8-azaspiro[4.5]decane-7,9-dion-8-yl)methyl]-
2-(2-pyrimidinyl)-2,3,4,6,7,8,9,9a-octahydro-1H-
pyrido[1,2-a]pyrazine By method C of Example 1, cis-7-(aminomethyl)-2-(2-pyrimidinyl)-2,3,4,6,7,8,9,9a-octahydro-H-pyrido-[1,2-a]pyrazine (142 mg, 0.57 retool) and 3,3-tetramethylenegluaric anhydride (96 mg, 0.57 mmol) were converted to 105 mg (46%) of present title product as colorless crystals from isopropyl alcohol, identical to the material prepared in Example 2.

EXAMPLE 6

(7S, 9aS) -2-(2-Pyrimidyl)-7-(succinimidomethyl)-
2,3,4,6,7,8,9,9a-octahydro-1H-pyrido[1,2-a]pyrazine A mixture of (7R,9aS)-7-(Aminomethyl)-2-(2-pyrimidinyl)-2,3,4,6,7,8,9,9a-octrahydro-1H-pyrido-[1,2-a]pyrazine (6.30 g, 0.025 mol) and succinic anhydride (2.80 g, 0.028 mol) in 280 ml of mixed xylenes (b.p. 139°–143° C.) was heated to 100° C., at which point dimethylformamide (4 ml) was added to affect complete solution. Using a Dean-Stark trap, the mixture was vigorously refluxed for two hours. The reaction solution was decanted from a tarry residue and concentrated in vacuo to amorphous solids, which were transferred to a well-stirred mixture of methylene chloride and water (250 ml of each) and the pH adjusted to 11 with 6N NaOH. The organic phase was separated, dried (Na$_2$SO$_4$), and concentrated in vacuo to a colorless foam (6.4 g). Crystallization of the entire sample from hot isopropyl alcohol (250 ml) afforded 4.7 g (56%) of present title product, mp 211°–212° C.; [alpha]$_D^{25}$=–35° (CH$_2$Cl$_2$).

HRMS 329.1809, calcd. 329.1854. The $^{13}$C-NMR was identical to that of the racemic product of Example 1.

Alternatively 5.0 mg (17%) of identical product, likewise crystallized from isopropanol, was prepared from (7S, 9aS)-7-(hydroxymethyl)-2-(2-pyrimidinyl)2,3,4,6,7,8,9,9a-octahydro[1,2-a]pyrazine (17.1 mg, 0.069 mol) by Method A of Example 1.

EXAMPLE 7 cis -7-(Pyrazolomethyl)-2-(2-pyridyl)-2,3,4,6,7,8,9,
9a-octahydro-1H-pyrido[1,2-a]pyrazine cis-7-(Methanesulfonyloxymethyl)-2-(2-pyridyl)2,3,4,6,7,8,9,9a-octahydro-1H-pyrido [1,2-a]pyrazine (350 mg, 1.0 mmol), pyrazole (439 mg, 6.5 mmol) and sodium carbonate (228 mg, 2.2 mmol) and 15 ml of acetonitrile were refluxed for 18 hours. The reaction mixture was cooled, stripped of solvent and the residue distributed between 20 ml each of CH$_2$Cl$_2$ and water. The well-stirred, 2-phase mixture was adjusted to pH 10 with saturated Na$_2$CO$_3$. The aqueous layer was extracted 1×20 ml from CH$_2$Cl$_2$. The organic layers were combined, dried (Na$_2$SO$_4$) and stripped to solids, which were flash chromatographed on 6 g of silica gel with ethyl acetate as eluant to yield 134 mg (42%) of title product as an amorphous solid. TLC Rf 0.43 (9:1 CH$_2$Cl$_2$:CH$_3$OH); HRMS 297.1962, calcd. 297.1957.

$^{13}$C-NMR (300 MHz, CDCl$_3$) delta 159.3, 147.9, 139.3, 137.4, 129.8, 113.1, 107.0, 104.9, 60.9, 56.6, 54.6, 53.1, 50.7, 45.2, 34.7, 25.0, 24.9.

PREPARATION 1

Dimethyl Pyridine-2,5-dicarboxylate

To a stirred slurry of 2,5-pyridinedicarboxylic acid (2407 g; 14.4 mol) in methanol (8.0 liter) at –5° to –10° C. thionylchloride (3430 g; 2.10 liters; 28 8 mol) was added dropwise while maintaining the temperature in the –5° to –10° C. range. After completing the addition, the reaction was allowed to warm to ambient temperature, and stirred for 18 hours. The resulting solution was concentrated in vacuo to a volume of 4 liters, and an equal volume of water was added. The pH of the well-stirred mixture was then adjusted to 10 with saturated aqueous sodium carbonate. Solids were removed by filtration. The organic layer of the filtrate was separated, washed with water (8 liters), and dried in vacuo to afford the title compound (2250 g; 80% yield) as an amorphous solid.

PREPARATION 2

Dimethyl cis- and trans-Piperidine-2,5-dicarboxylate Acetate

The product of the preceding Preparation (2250 g; 11.53 mol) in glacial acetic acid (25 liters) was hydrogenated in the presence of 57 g platinum oxide as catalyst at 3.52 kg/cm$^2$ pressure for 18 hours. The catalyst was recovered by filtration, and the filtrate concentrated in vacuo to afford a mixture of title acetate salts as a viscous amber syrup (2300 g, 100% yield), sufficiently pure for use directly in the next step.

PREPARATION 3

Dimethyl cis- and trans-1-(Cyanomethyl)piperidine-2,5-dicarboxylate

A well-stirred mixture of title product of the preceding Preparation (3000 g, 11.53 mol), chloroacetonitrile (1.00 kg; 13.25 mol; 1.1 equivalents), sodium carbonate (8.00 kg; 75.5 mol; 6.5 equivalents), and potassium iodide (320 g; 1.90 mol; 0.17 equivalents) in methylisobutyl ketone (36 liters), was refluxed vigorously for 18 hours. The reaction was cooled to room temperature, and solids were removed by suction filtration. The filter cake was extracted, first with methyisobutyl ketone (12 liters), and then with methylene chloride (30 liters). The original filtrate and both filtered extracts were combined and then concentrated in vacuo to afford the mixed title products (1400 g; 51% yield) as an amber oil.

PREPARATION 4

Methyl cis-1-Oxo-2,3,4,6,7,8,9,9a-octahydro-1H-Pyrido[1,2-a]pyrazine-7-carboxylate Title product of the preceding Example (60.0 g, 0.25 mol) in methanol (1 liter) and ethyl acetate (0.4 liter) was hydrogenated over Raney nickel (washed with water to pH 9 on a filter funnel; 93 g water wet) at 3.52 kg/cm$^2$ pressure for 18 hours. The catalyst was filtered, and the filtrate was concentrated in vacuo to an oil. Overnight crystallization from a methylene chloride/isopropyl ether (90 ml/120 ml respectively) afforded exclusively the desired cis isomer (title product) as colorless crystals, mp 166°–168° C. (dec.), (24.99 g; 47% yield); HRMS 212.1156, calcd. 212.1162.

$^{13}$C-NMR (300 MHz, CDCl$_3$) delta 173.9, 171.2, 64.8, 64.7, 56.3, 56.2, 51.7, 50.8, 40.6, 39.5, 25.0, 24.4

PREPARATION 5 cis-7-Hydroxymethyl-2,3,4,6,7,8,9,9a-octahydro-1H-pyrido[1,2-a]pyrazine

A flame-dried flask fitted with a magnetic stirrer, condenser, and nitrogen inlet was charged with a slurry of lithium aluminum hydride (14.88 g, 0.46 mol) in 500 ml of dry tetrahydrofuran. Title product of the preceding Preparation (53.61 g, 0.25 mol) was added portionwise, in solid form, to the well-stirred mixture over a one hour period. The mixture was then refluxed under nitrogen for 18 hours. After cooling to 15° C. the reaction was quenched by cautious dropwise addition of water (100 ml). The mixture was then filtered, and the filter cake was washed with 150 ml of tetrahydrofuran. The filtrate was concentrated in vacuo to a solid, which was extracted three times with one liter portions of methylene chloride. The tetrahydrofuran and methylene chloride extracts were concentrated in vacuo to afford the title compound (42.06 g, 97.8% yield) as an amorphous solid. HRMS 170.14 13, calcd. 170. 1419.

$^{13}$C-NMR (300 MHz, CDCl$_3$) delta 65.6, 62.6, 57.8, 56.0, 51.8, 45.8, 34.7, 26.4, 26.0

PREPARATION 6 cis-7-Hydroxymethyl-2-(2-pyrimidinyl)-2,3,4,6,7,8,9,9a-octahydro-1H pyrido[1,2-a]pyrazine A solution consisting of title product of the preceding preparation (19.7 g; 0.12 mol), sodium carbonate (30.45 g; 0.29 mol) and 2-chloropyrimidine (13.6 g; 0.12 mol) in water (150 ml) was stirred and heated at 95° C. for 14 hours. The reaction mixture was cooled, and then extracted with 200 ml of methylene chloride. The organic extract was washed with water and then with brine (200 ml of each), stirred with activated carbon, filtered, dried (anhydrous sodium sulfate, and concentrated to an amber oil. Crystallization of the entire sample from methylene chloride/hexane (45 ml/150 ml, respectively) afforded 21.5 g (76.7% yield) of the title compound as colorless crystals, mp 135°–136° C. HRMS 248.1622, calcd. 248.1637. TLC Rf 0.3 (CH$_2$Cl$_2$:CH$_3$OH 9:1).

$^{13}$C-NMR (300 MHz, CDCl$_3$) delta 161.2, 157.6, 109.7, 65.5, 60.9, 57.3, 54.8, 48.9, 43.4, 34.8, 26.1, 25.8

PREPARATION 7 cis-7-(Methanesulfonyloxymethyl)-2-(2-pyrimidinyl)-2,3,4,6,7,8,9,9a-octahydro-1-pyrido[1,2-a]pyrazine To a well-stirred solution of the title product of the preceding Preparation (1.5 g; 6.0 mmol) and triethylamine (1.68 ml, 12 mol) in methylene chloride (28 ml) chilled to 5° C., a solution of methanesulfonyl chloride (0.70 ml; 9.0 mmol) in methylene chloride (7 ml) was added dropwise over 15 minutes. Within 10 minutes of stirring (5° C.) following the methane-sulfonylchloride addition, inspection of a reaction aliquot by thin layer chromatography (silica gel plates; elution with methylene chloride/methanol=9.1 by volume; UV detection) showed complete reaction. Water (50 ml) was added to the reaction mixture, and the pH of the well-stirred mixture was adjusted to 9.5 with saturated sodium carbonate. The organic phase was separated, washed five times with 150 ml portions of water, dried (anhydrous sodium carbonate), and concentrated in vacuo to afford the title compound (1.87 g, 95.4% yield), sufficiently pure for use in the next step without further purification. The entire sample was dissolved in 3 ml of hot methylene chloride, to which hexane was added dropwise (ca 3 ml) until the solution became turbid. Stirring for one hour afforded 1.10 g of crystalline title product (colorless crystals), mp 141°–142° C.

$^{13}$C-NMR (250 MHz, CDCl$_3$) delta 161.3, 157.6, 109.7, 71.1, 60.8, 55.7, 54.6, 48.9, 43.5, 36.9, 33.4, 24.7, 24.2

PREPARATION 8 cis-7-Hydroxymethyl-2-(2-pyridyl)-2,3,4,6,7,8,9,9a-octahydro-1H-pyrido[1,2-a)pyrazine A mixture consisting of title product of Preparation 5 (9.10 g; 53.4 mmol), sodium carbonate (14.1 g; 0.13 mol), and 2-bromopyridine (25.5 ml; 42.3 g; 0.27 mol) in isoamylalcohol (25 ml) was refluxed for 72 hours. The reaction was filtered while hot, and the filter cake washed with 50 ml of methylene chloride. The filtrate was concentrated in vacuo to an oil, which was taken up in 100 ml ethyl acetate. An equal volume of water was added, and the pH of the well-stirred mixture was adjusted to 11.5 (saturated sodium carbonate). The organic phase was separated, treated with activated carbon, dried (anhydrous sodium sulfate), and concentrated in vacuo to an oil. Flash chromatography of the entire sample (125 g silica gel, 32–63 mesh; elution with methylene chloride/methanol=97:3 by volume) with TLC monitoring of fractions [product R$_f$=0.26 (methylene chloride:methanol 9:1 in volume), detection by U.V. and Dmgendorf's spray] afforded 7.50 g (56.6% yield) of the title compound as a pale yellow amorphous solid.

$^{13}$C-NMR (300 MHz, CDCl$_3$) delta 159.1, 147.8, 137.4, 113.2, 107.0, 65.8, 60.7, 57.3, 54.4, 50.6, 45.0, 34.7, 26.2, 26.0

PREPARATION 9 cis-7-(Methanesulfonyloxymethyl)-2-(2-pyridyl)-2,3,4,6,7,8,9,9a-octahydro-1H-pyrido [1,2-a]pyrazine By the method of Preparation 7, the title product of the preceding Example (240 mg, 0.97 mmol) was converted to present title product (0.30 g, 94.7%) as a colorless oil. TLC Rf 0.34 (ethyl acetate). RMS 325. 1475, calcd. 325. 1460.

$^{13}$C-NMR (250 MHz, CDCl$_3$) delta 159.2, 147.9, 137.5, 113.2, 107.1, 71.2, 60.7, 55.7, 54.6, 50.7, 45.2, 37.0, 33.5, 24.9, 24.2

PREPARATION 10 cis-7-(Pthalimido)methyl-2-(2-pyrimidinyl)-2,3,4,6,7,8,9,9a-octahydro-1H-pyrido[1,2-a]pyrazine Method A By Method A of Example 1, phthalimide (4.13 g, 36.5 mmol) and the title product of Preparation 7 (7.93 g, 2.43 mmol) was converted to present title product, as colorless crystals from warm isopropyl alcohol (1.86 g, 20%); mp 161°–162° C. HRMS 377.1815, calcd. 377. 1852.

$^{13}$C-NMR (300 MHz, CDCl$_3$) delta 168.4, 161.3, 157.6, 133.8, 132.0, 123.0, 109.5, 61.0, 57.8, 54.7, 48.9, 43.5, 39.8, 32.9, 24.8, 24.4

Method B

By Method B of Example 1, phthalimide (147 mg, 1.0 mmol) and the title product of Preparation 6 (248 mg, 1.0 mmol) were converted to 31 mg (9.5%) of identical title product.

PREPARATION 11 cis-7-(Azidomethyl)-2-(2-pyrimidyl)-2,3,4,6,7,8,9,9a-octahydro-1H-pyrido [1,2-a]pyrazine Title product of Preparation 7, (57.1 g; 0.175 mol) and sodium azide (75 g; 1.1 mol) in dry dimethylformamide (500 ml) was stirred 17 hours at 100° C. (oil bath). Stirring and heating was stopped, and the slurry of excess sodium azide was allowed to settle. The supernatant was carefully decanted, and then concentrated in vacuo to a light yellow oil. The residual sodium cake was extracted twice with 500 ml portions of methylene chloride. The oil was dissolved in the combined methylene chloride extracts. An equal volume of water was added, and the pH of the well-stirred mixture adjusted to 11.5 (6N sodium hydroxide). The organic phase was separated, dried (anhydrous sodium sulfate), and concentrated in vacuo to afford 48.2 g of title compound as a light-yellow oil. TLC Rf 0.53 (ethylacetate). HRMS 273.1735, calcd. 273.1705.

$^{13}$C-NMR (250 MHz, CDCl$_3$) delta 161.3, 157.6, 109.6, 60.9, 56.7, 54.6, 52.8, 48.9, 43.5, 33.7, 25.3, 24.7

PREPARATION 12 cis-7-(Aminomethyl)-2-(2-pyrimidinyl)-2,3,4,6,7,8,9,9a-octahydro-1-pyrido[1,2-a]pyrazine Method A A suspension of the title product of Preparation 10 (1.86 g; 4.9 mmol) in ethanol (15 ml) and anhydrous hydrazine (0.156 ml; 158 mg; 4.9 mmol) was refluxed for 2.5 hours. The mixture was concentrated in vacuo to an oil. Concentrated hydrochloric acid (10 ml) was added, and the mixture refluxed for 3.5 hours. The reaction was filtered and the filtrate was concentrated in vacuo to a solid, all of which was dissolved in 15 ml of water and the pH adjusted to 10.0 (6N sodium hydroxide). The basic solution was extracted with 5×50 ml of methylene chloride, and the organic extracts combined, dried (anhydrous sodium sulfate) and concentrated in vacuo to afford 1.07 g (88%) of present title product as an amber oil. TLC Rf 0.50 (CH$_2$Cl$_2$:CH$_3$OH:conc. NH$_3$ 3:1:0.3). HRMS 247.1784, calcd. 247. 1787.

$^{13}$C-NMR (300 MHz, CDCl$_3$) delta 161.3, 157.6, 109.5, 61.1, 57.0, 54.9, 48.9, 43.4, 42.9, 36.6, 25.6, 24.9

Method B

A solution of the title product of the preceding Preparation (48.0 g; 0.176 mol) in 800 ml of ethanol and 70 ml of ethyl acetate was hydrogenated at a pressure of 3.5 kg/cm$^2$ in the presence of 24 g of 5% palladium-on-carbon catalyst for 2 hours. Filtration of the catalyst and in vacuo concentration of the filtrate afforded 34.8 g (80%) of title compound as a colorless oil which crystallized upon standing, with the product of method A.

PREPARATION 13 cis-7-(Pthalimido)methyl-2-(2-pyridyl)-2,3,4,6,7,8,9,9a-octahydro-1H-pyrido [1,2-a]pyrazine By method B of Example 1, pthalimide (0. 595 g, 4.1 mmol) and title product of Preparation 8 (1.00 g, 4.1 mmol) were converted to 1.02 g (67%) of present title product as colorless crystals from isopropanol, mp 167°–168° C. HRMS 3 76.1900, calcd. 376.1900.

$^{13}$C-NMR (300 MHz, CDCl$_3$) delta 168.6, 159.3, 147.9, 137.4, 133.9, 132.1, 123.2, 113.0, 107.0, 60.9, 57.8, 54.7, 50.7, 45.1, 39. 9, 33.0, 24.9, 24.6

PREPARATION 14 cis-7-(Azidomethyl)-2-(2-pyridyl)-2,3,4,6,7,8,9,9a-octahydro-1H-pyrido[1,2-a]pyrazine By the method of Preparation 11, title product of Preparation 9 (1.0 g, 3.06 mmol) was converted to 0.70 g (84%) of present title product as a colorless oil. HRMS 272.1739, calcd. 272.1750

$^{13}$C-NMR (300 MHz, CDCl$_3$) delta 159.2, 147.7, 137.2, 112.8, 106.8, 60.9, 56.9, 54.8, 50.5, 44.9, 43.1, 37.0, 25.6, 25.0

PREPARATION 15 cis-7-(Aminomethyl)-2-(2-pyridyl)-2,3,4,6,7,8,9,9a-octahydro-1H-pyrido[1,2-a]pyrazine By Method A of Preparation 12, title product of Preparation 13 (0.484 g, 1.29 mmol) was converted to 0.311 g (98%) of present title product as a colorless, viscous oil. TLC Rf 0.51 (CH$_2$Cl$_2$:CH$_3$OH: conc. NH$_3$3:1:0.3). HRMS 246.1861, calcd. 246.1844.

Identical product (0.60 g, 95%) was prepared from title product of the preceding Preparation (0.70 g, 2.6 mmol) by Method B of Preparation 12.

PREPARATION 16

(7R-9aS)-7-(Aminomethyl)-2-(2-pyrimidinyl)-2,3,4,6,7,8,9,9a-octahydro-1H-pyrido[1,2-a]pyrazine To a solution of the title product of Preparation 12 (33.54 g, 0.136 mol) in 1.44 l of near-boiling isopropanol, (–)-mandelic acid (20.63 g, 0.136 mol) was added with stirring to effect total dissolution. The stirred solution was allowed to cool slowly to ambient temperature; and 24 hours later a heavy crystalline mass was isolated by suction filtration, and dried in vacuo. The entire sample was dissolved in 1.85 l of hot isopropanol, and the resulting solution was allowed to cool to ambient temperature, and stir at that temperature for 72 hours, during which time, a heavy colorless crystalline mass formed. [14.0 g, 51.7% yield of the (–)-mandelic acid salt of present title product, mp 202°–203° C. (dec.)]. The entire sample was dissolved in water (200 ml). An equal volume of methylene chloride was added, and the pH of the well-stirred mixture was adjusted to 9.5 with 6N NaOH. The organic phase was separated, dried, and concentrated in vacuo to afford 6.30 g (37.6%) of present title product as a colorless solid.

[alpha]$_D^{25}$=36.7° in methylene chloride (C=0.0337 g/ml)]

The title product of the preceding Preparation is resolved by the same method to form (7R, 9aS)-7-(Aminomethyl)-2-(2-pyridyl)-2,3,4,6,7,8,9,9a-octahydro-1H-pyrido [1,2-a] pyrazine.

PREPARATION 17

(7S-9aS)-7-(Acetoxymethyl)-2-(2-pyrimidinyl)-2,3,4,5,6,7,8,9,9a-octahydro-1-pyrido[1,2-a]pyrazine To title product of the preceding Preparation (180.4 mg, 0.73 mmol) in 2 ml of CHCl$_3$ was added acetic acid (0.125 ml, 2.19 mmol) and isoamyl nitrite (0.108 ml, 0.802 mmol). The resulting mixture was refluxed for 4 hours, cooled, diluted with 25 ml CHCl$_3$ and then 10 ml H$_2$O, and adjusted to pH 10 with saturated Na$_2$CO$_3$. The aqueous layer was separated and extracted with 20 ml CH$_2$Cl$_2$. The organic layers were combined, treated with activated carbon, dried (Na2SO$_4$) and stripped to yield 188.5 mg of an oil, which was chromatographed on silica gel using 500 ml of 3:2 ethyl acetate:hexane as eluant, monitored by TLC (ethyl acetate). Desired product fractions (Rf 0.30) were combined and stripped to yield 58.5 mg (28%) of present title product.

[alpha]$_D^{25}$=–35.9° (CH$_2$Cl$_2$). HRMS 290.1752, calcd. 290.1742.

$^{13}$C-NMR (300 MHz, CDCl$_3$) delta 171.2, 161.4, 157.7, 109.6, 65.5, 61.0, 56.4, 54.8, 48.9, 43.5, 33.0, 24.9, 24.7, 21.1

By the same method the 2-(2-pyridyl) derivative of the preceding Preparation is converted to (7S, 9aS-7-(acetoxymethyl)-2-(2-pyridyl)-2,3,4,6,7,8,9a-octahydro-1H-pyrido[1,2-a]pyrazine.

PREPARATION 18

(7S, 9aS)-7-(Hydroxymethyl)-2-(2-pyrimidinyl)-2,3,4,6,7,8,9,9a-octahydro-1-pyrido[1,2-a]pyrazine Title product of the preceding Preparation (51.4 mg, 0.177 mmol) was dissolved in 1 ml of 1:1 H$_2$O:CH$_3$OH, and 6N NaOH (0.06 ml, 3.6 mmol) was added. After stirring for 3 hours, the mixture was stripped of CH$_3$OH, the aqueous residue diluted with 25 ml CH$_2$Cl$_2$ and 10 ml H$_2$O, and the pH of the 2 phase system adjusted to 10. The separated aqueous layer was extracted 2×10 ml CH$_2$Cl$_2$, and the organic layers combined, dried (Na$_2$SO$_4$), stripped and the residue crystallized from CH$_2$Cl$_2$ and isopropyl ether to yield 27 mg of title product mp 160°–162° C.

[alpha]$_D^{25}$=–34.2° (CH$_2$Cl$_2$) HRMS 248.1647, calcd. 248.1638.

By the same method, the pyridyl analog of the preceding Preparation is converted to (7S, 9aS)-7-(hydroxymethyl)-2-(2-pyridyl)-2,3,4,6,7,8,9,9a-octahydro-1H-pyrido[1,2-a] pyrazine.

PREPARATION 19

(7S-9aS)-7-(Methanesulfonyloxymethyl)-2-(2-pyrimidinyl)-2,3,4,6,7,8,9,9a-octahydro-1H-pyrido[1,2-a]pyrazine By the method of Preparation 9, the title product of the preceding Preparation (20.5 mg) was converted to present title product in essentially quantitative yield. TLC Rf 0.50 (9:1CH$_2$Cl$_2$:CH$_3$OH).

By the same method, the pyridyl analog of the preceding Preparation is converted to (7S, 9aS)-7-(methanesulfonyloxymethyl)-2-(2-pyridyl)-2,3,4,6,7,8,9,9a-octahydro-1H-pyrido[1,2-a]pyrazole.

I claim:

1. A method of treating substance abuse or addiction in a human, wherein said substance abuse or addiction is selected from the group consisting of alcohol and nicotine abuse or addiction, which comprises administering to said human an effective amount of a racemic or optically active compound of the formula

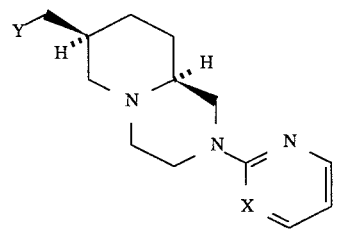

or pharmaceutically acceptable acid addition salt thereof, wherein

X is N or CH;

Y is

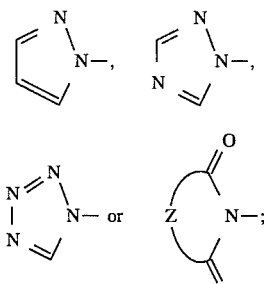

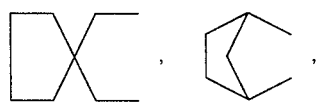

SCH$_2$, OCH$_2$, —Y$^1$(CH$_2$)$_n$—wherein the (CH$_2$)$_n$ portion of said —Y$^1$(CH$_2$)$_n$— is optionally substituted with 1 or 2 methyl groups;

n is 1 or 2; and

Y$^1$ is CH$_2$, NH or NCH$_3$.

2. A method of claim 1 wherein X is N.

3. A method of claim 1 wherein Y is

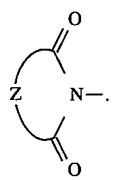

4. A method of claim 3 wherein X is N.

5. A method of claim 1 wherein the compound is optically active.

6. A method of claim 2 wherein the compound is optically active.

7. A method of claim 4 wherein the compound is optically active.

8. A method of claim 4 wherein the compound is racemic and Z is —$Y^1(CH_2)_n$— wherein the $(CH_2)_n$ portion of said —$Y^1(CH_2)_n$— is optionally substituted with 1 to 2 methyl groups.

9. The method of claim 8 wherein Z is $Y^1(CH_2)_n$, $Y^1$ is $CH_2$ and n is 1.

10. A method of claim 7 wherein Z is —$Y^1(CH_2)_n$— wherein the $(CH_2)_n$ portion of said —$Y^1(CH_2)_n$— is optionally substituted with 1 to 2 methyl groups.

11. The method of claim 10 wherein Z is $Y^1(CH_2)_n$, $Y^1$ is $CH_2$ and n is 1.

12. A method of claim 3 wherein Z is $SCH_2$ or $OCH_2$.

13. A method of claim 3 wherein Z is $Y^1(CH_2)_n$ and $Y^1$ is NH or $NCH_3$.

14. A method of claim 1 wherein Y is

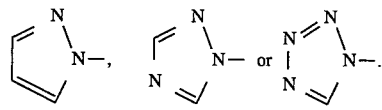

15. A method of claim 1 wherein X is CH.

16. A method of claim 15 wherein Y is

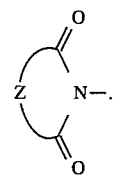

17. The method of claim 1 wherein said substance abuse or addiction is alcohol abuse or addiction.

18. The method of claim 1 wherein said substance abuse or addiction is nicotine abuse or addiction.

* * * * *